(12) United States Patent
Djurling et al.

(10) Patent No.: US 8,521,307 B2
(45) Date of Patent: Aug. 27, 2013

(54) IMPLANTABLE MRI COMPATIBLE MEDICAL LEAD

(75) Inventors: Henrik Djurling, Järfälla (SE); Kenneth Dahlberg, Stockholm (SE); Mikael Forslund, Stockholm (SE); Patrik Forsström, Järfälla (SE); Leda Henriquez, Vällingby (SE); Linn Olsen, Sundbyberg (SE); Olof Stegfeldt, Älta (SE); Åke Sivard, Solna (SE)

(73) Assignee: St. Jude Medical AB, Jarfalla Se (SE)

( * ) Notice: Subject to any disclaimer, the term of this patent is extended or adjusted under 35 U.S.C. 154(b) by 62 days.

(21) Appl. No.: 13/262,551

(22) PCT Filed: Jul. 10, 2009

(86) PCT No.: PCT/SE2009/000364
§ 371 (c)(1),
(2), (4) Date: Sep. 30, 2011

(87) PCT Pub. No.: WO2010/114432
PCT Pub. Date: Oct. 7, 2010

(65) Prior Publication Data
US 2012/0035693 A1    Feb. 9, 2012

(30) Foreign Application Priority Data
Mar. 31, 2009  (WO) ............... PCT/SE2009/000169

(51) Int. Cl.
*A61N 1/05*  (2006.01)
(52) U.S. Cl.
USPC ............................................. 607/127

(58) Field of Classification Search
USPC ........................................ 607/126, 127, 131
See application file for complete search history.

(56) References Cited

U.S. PATENT DOCUMENTS

| | | |
|---|---|---|
| 4,463,765 A | 8/1984 | Gold |
| 4,667,686 A | 5/1987 | Peers-Travarton |
| 5,217,010 A | 6/1993 | Tsitlik et al. |
| 5,741,321 A | 4/1998 | Brennen |
| 6,295,475 B1 | 9/2001 | Morgan |
| 6,606,522 B2 | 8/2003 | Schell |
| 6,944,489 B2 | 9/2005 | Zeijlemaker et al. |
| 7,174,219 B2 | 2/2007 | Wahlstrand et al. |
| 7,287,995 B2 | 10/2007 | Stein et al. |

(Continued)

*Primary Examiner* — George Evanisko

(57) ABSTRACT

A medical implantable lead is adapted to be implanted into a human or animal body for monitoring and/or controlling of an organ inside the body, and has in a distal end, a combined fixation means and electrode member in form of a helix, which is rotatable in relation to the lead and extendable out from the distal end by rotation of a tubular torque transferring member. The helix is electrically connected to a connector in the proximal end by at least one electrically conducting wire, which is formed as an electrically conducting coil, which is separate from the tubular torque transferring member and that includes one or more individual wires each having an electrically conducting wire core and a surrounding electrically insulating layer. The tubular torque transferring member has no electrically conducting function to or from the helix. The lead is arranged such that the electrical connection between the helix and the conducting wire is always maintained regardless of the rotational position of the helix while no electrical connection is present between the helix and the tubular torque transferring member although the helix is rotatable by the tubular torque transferring member.

11 Claims, 5 Drawing Sheets

(56) References Cited

U.S. PATENT DOCUMENTS

| | | |
|---|---|---|
| 7,363,090 B2 | 4/2008 | Halperin et al. |
| 7,657,326 B2 | 2/2010 | Bodner et al. |
| 2005/0090884 A1 | 4/2005 | Honeck |
| 2007/0179577 A1 | 8/2007 | Marshall et al. |
| 2007/0179582 A1 | 8/2007 | Marshall et al. |
| 2007/0255377 A1* | 11/2007 | Marshall et al. .............. 607/119 |
| 2007/0299493 A1* | 12/2007 | Osypka ......................... 607/127 |
| 2008/0288040 A1 | 11/2008 | Eckerdal et al. |

* cited by examiner

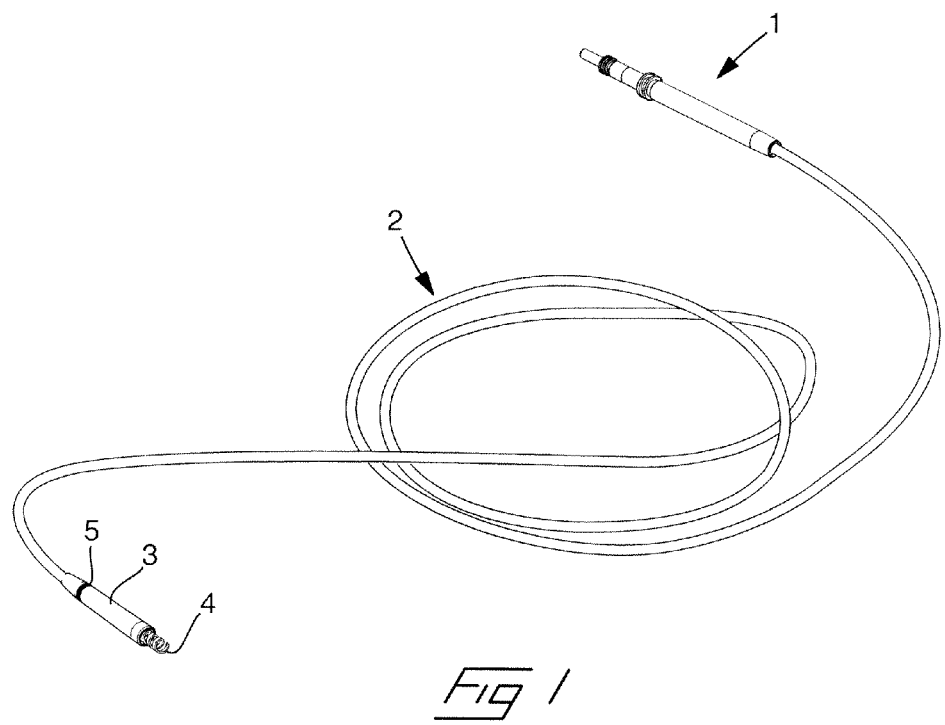
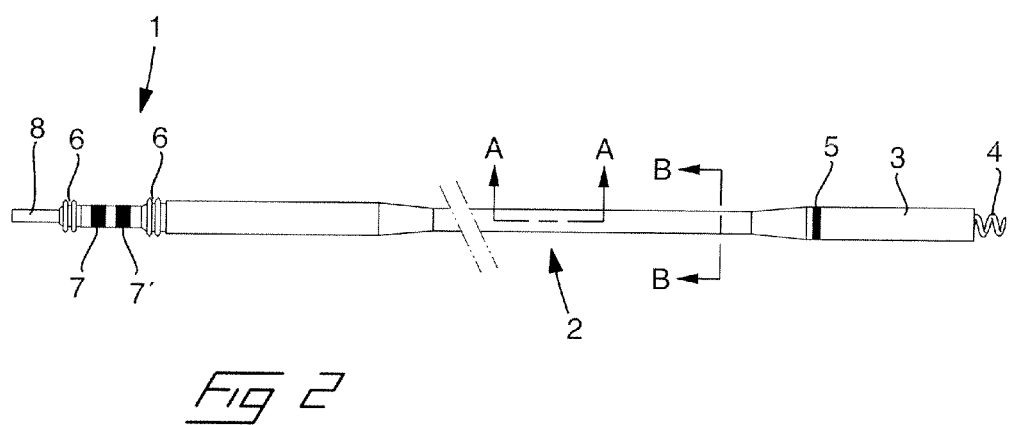

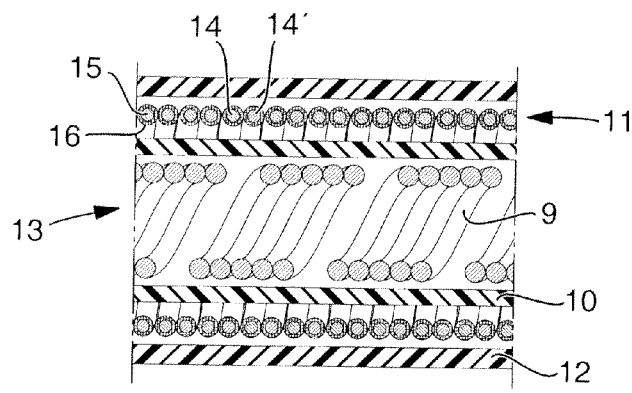
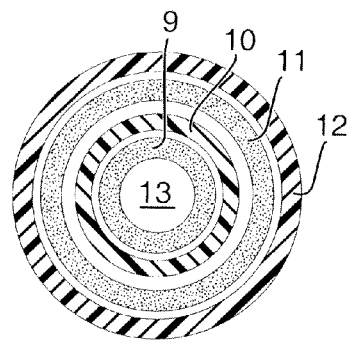
Fig 3
Fig 4
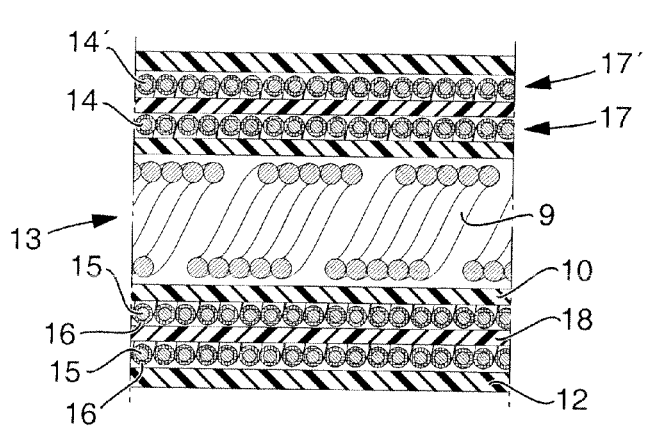
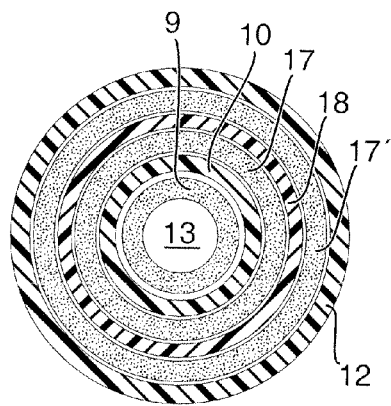
Fig 5
Fig 6

IMPLANTABLE MRI COMPATIBLE MEDICAL LEAD

BACKGROUND OF THE INVENTION

1. Field of the Invention

The present invention relates to a medical implantable lead of the kind being adapted to be implanted into a human or animal body for monitoring and/or controlling of an organ inside the body, comprising in a distal end a combined fixation means and electrode member in form of a helix, which is rotatable in relation to the lead and extendable out from the distal end by rotation of a tubular torque transferring member being connected to a rotatable control member in a proximal end of the lead, and which is adapted to fixate the distal end of the lead to the organ by being screwed into the tissue by rotation of the control member and the tubular torque transferring member, wherein the helix is electrically connected to a connector in the proximal end by means of at least one electrically conducting wire

2. Description of the Prior Art

It is well known in the art to use a medical implantable lead of the above kind to monitor and/or control the function of an organ inside a human or animal body, for example to monitor and/or control a heart by means of a monitoring and/or controlling device in form of a pacemaker or cardiac defibrillator connected to the proximal end of the lead. The medical implantable lead is provided with at least one electrical conductor, in form of a coil having one or more helically formed electrically conducting wires, sometimes also referred to as filars, which electrically connects one or more connectors arranged in the proximal end of the lead with one or more electrodes in its distal end. At least one of the electrodes is adapted to be in contact with the tissue of the organ for receiving and/or transmitting electrical signals from and/or to the organ and transmit them, through the electrically conducting coil, to the monitoring and/or controlling device connected to a connector in the proximal end of the lead. For attaching the distal end of the lead to the organ, the lead is provided with a helix, which can be rotatably extended out from the distal end of the lead and accordingly screwed into the tissue of the organ. To accomplish the rotation of the helix, it is mechanically connected to the innermost one of the electrically conducting coils, which accordingly has to be rotatable in relation to the lead as well as be sufficiently rigid to be able to transmit the required torque from the proximal to the distal end. The helix also functions as an electrode, which is penetrated into and embedded within the tissue. The helix may also be provided with one or more additional electrodes separate from the helix and e.g. be formed as a contact electrode, abutting against a surface of the organ, or be formed as a so called indifferent electrode which is surrounded by body fluids such as blood.

Normally, such medical implantable leads are not considered to be compatible with Magnetic Resonance Imaging (MRI), i.e. persons or animals having such a lead implanted into the body, are excluded from being examined by MRI-scanning. This is due to the fact that the electromagnetic field, that is generated during the MRI-scanning, will induce a current in the conductor, which connects the one or more electrodes in the distal end of the medical implantable lead with the monitoring and/or controlling device in the proximal end of the lead. This induced current may cause heating at an electrode being in contact with the tissue of the organ. If the heating is too high, there is a risk that this will cause damages to the tissue. However, the use of MRI-scanning for diagnostics is growing extensively and an increasing number of the population having a lead implanted would benefit from MRI-scans. It is thus desirable to reduce any heating at or close to the lead tip to acceptable and safe levels to allow MRI-scanning also of persons or animals having such a lead implanted.

It is known in the art to provide such medical implantable leads with an electrical shielding, in form of a tube of braided wires, which surrounds the coil and which in its proximal end normally is connected to the casing of the monitoring and/or controlling device. However, such shielded medical implantable leads are associated with several disadvantages. On the one hand, the braided shielding will give the medical implantable lead an increased thickness as well as increased rigidity, which normally is not desirable. On the other hand, it has appeared that such a braided shielding cannot prevent the induction of electrical current to the coiled conductor in a degree that is sufficient to, without risk, expose an individual, having an implanted lead, to a MRI-scanning.

U.S. Pat. No. 5,217,010 discloses a way to reduce heating caused by induced current from MRI-scanning by placing inductors close to the electrodes to limit currents through the electrodes. Such a prior art medical implantable lead comprises passive electronic components, which contribute to making the lead more complex and thus more costly to manufacture.

SUMMARY OF THE INVENTION

It is an object of the invention to provide a medical implantable lead, which in a simple and cost-effective way reduces the induction of current from an electromagnetic field into the electrically conducting coil. At least this object is achieved by a medical implantable lead according to claim 1.

Accordingly, the basis of the invention is the insight that the above object may be achieved by separating the function of effecting rotation and extending of the helix out from the distal end of the lead from transmitting the electrical signals between the helix and where appropriate the one or more further electrodes in the distal end and the one or more connectors in the proximal end, i.e. to split these functions on separate members within the lead. More precisely, the function of transmitting a torque from the proximal end to the distal end for effecting rotation and extending of the helix out from the distal end, is effected by an inner tubular torque transferring member, which has no electrically conducting function to or from the helix, whereas the electrically conducting function to and from the helix is effected by a separate electrically conducting coil being formed of one or more helical wires. Each wire is moreover coated with an electrically insulating layer, such that the coil will form an inductor, which will allow the low frequency signals between the electrode and the monitoring and/or controlling device to pass through without being exposed to especially high impedance. On the other hand, for induced current from high frequency electromagnetic fields, such as fields from MRI-scanning typically operating at 64 or 128 MHz, the impedance in the electrically conducting coil will be very high which to a large extent will restrain induced high frequency currents. Since the inner tubular torque transferring member is mechanically connected to the helix but has no electrically conducting function to and from the helix, whereas the electrically conducting coil arranged outside of the tubular torque transferring member is not adapted to mechanically transfer any torque to the helix, the one or more conducting wires in the electrically conducting coil are arranged to always maintain the electrical connection between a connector in the proximal end and the helix in the distal end irrespective of the rotated position of the tubular torque transferring member and the helix.

Within this overall idea, the invention may be altered and modified in many different ways. For example, the tubular torque transferring member may optionally be formed as a flexible tube or as a helical coil of one or more threads or wires. It may also optionally be formed of an electrically insulating or a conducting material. In the former case no special measures has to be taken for insulating the tubular torque transferring member electrically from the helix and possibly also from the connector in the proximal end, such as may have to be done in case the tubular torque transmitting member is formed of an electrically conducting material.

Also, the electrical connection between the electrically conducting coil and the helix may be maintained in many different ways. For example, it is within the scope of the invention, however not described and illustrated hereinafter as an exemplified embodiment, that the electrically conducting coil may be simultaneously rotated with the tubular torque transferring member. With such an arrangement the connection between the helix and the electrically conducting coil can easily be arranged and maintained, for example by means of an electrically conducting wire from the coil to the helix, since the helix and the electrically conducting coil will not be mutually movable in relation to each other.

Another possible solution is to arrange, as in a hereinafter described and illustrated first embodiment, the connection between the electrically conducting coil and the helix by means of a sliding electrical contact.

In a second described and illustrated embodiment, a proximal end of one or more helically wound wires is attached to a non rotating coupling member, to which the electrically conducting coil is attached, and a distal end of the helically wound wires is attached to a shaft which is rotatable and displaceable journaled inside an inner bore of the coupling and which carries the helix. The direction of thread of the helically wound wires is contrary to the direction of rotation when extending the helix, such that when the shaft and helix are rotated by means of the tubular torque transferring member, the helically wound wires are extended and at the same time rotated contrary to their direction of thread. In this way the diameter reduction due to the extension of the helically wound wires are more or less counteracted by the diameter increment due to the rotation contrary to the direction of thread. An alternative embodiment is to, instead of winding the helically wound wires in a large coil around the axis of the shaft, wind them in small coils in parallel to each other and the axis of the shaft, as described and illustrated hereinafter in a third embodiment of the invention. Normally, it is preferred that the wires of the helically wound wires are provided with a surrounding electrically insulating layer for reason of MRI-compatibility, as the electrically conducting coil, and to prevent electrical contact with other electrically conducting parts of the lead, such as a protecting sleeve formed header around the distal end of the lead.

The embodiments described and illustrated hereinafter are given solely for exemplifying reasons and are not intended to be comprehensive. Accordingly, many other embodiments could be conceivable within the scope of the invention. For example one or more wires arranged between the electrically conducting coil and the helix, which have sufficient slack to be able to take up the increased distance due to rotation and extending of the helix.

BRIEF DESCRIPTION OF THE DRAWINGS

FIG. 1 is a perspective view of a medical implantable lead.

FIG. 2 is a view in an enlarged scale of the lead in FIG. 1 in a shortened state showing only the proximal and the distal ends of the lead.

FIG. 3 is a longitudinal section along the line A-A in FIG. 2 of a portion of a medical implantable lead according to the invention.

FIG. 4 is a cross section along the line B-B in FIG. 2 of the lead according to FIG. 3.

FIG. 5 is a longitudinal section along the line A-A in FIG. 2 of a portion of a medical implantable lead according to the invention.

FIG. 6 is a cross section along the line B-B in FIG. 2 of the lead according to FIG. 5.

DESCRIPTION OF THE PREFERRED EMBODIMENTS

Figure 7:
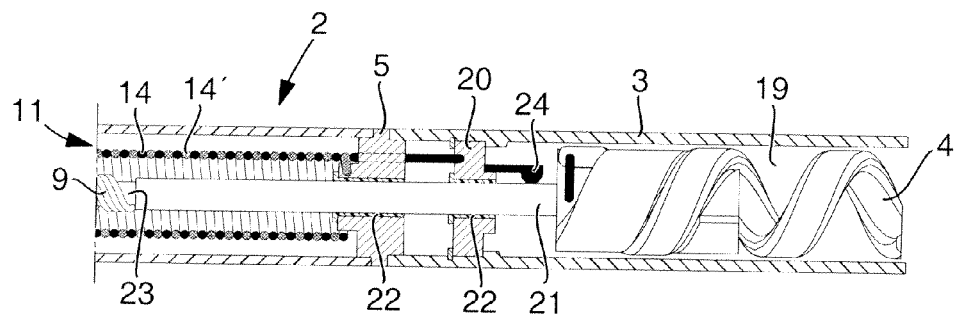
FIG. 7 is a longitudinal section through a distal portion of the medical implantable lead, illustrating a first embodiment of the electrical connection to the electrodes as well as the mechanical connection to the helix, which has the helix in a retracted state.

Reference is first made to FIG. 1, in which is illustrated a medical implantable lead according to the invention in a perspective view. The lead (lead body) includes a connecting structure 1 in a proximal end for connection to e.g. a pacemaker or the like (not shown), an intermediate flexible lead part 2, and a so called header 3 in a distal end. The header is provided with a helix 4, which can be screwed out in the axial direction of the lead from a cavity in the distal end of the header. The helix has the function of attaching the distal end of the lead to the heart, by being screwed into the tissue, and also functions as an electrode for receiving and/or transmitting electrical signals from and to the tissue, respectively. The header is also provided with a second electrode, a so called indifferent electrode 5, which is formed as a ring and positioned a small distance from the distal end and has the purpose of forming a complete current path together with the helix.

The proximal and the distal ends of the lead according to FIG. 1 are illustrated in an enlarged scale in the shortened representation of the lead in FIG. 2. The helix 4 for fixation of the distal end of the lead to tissue as well as for function as an electrode is shown in an extended state. However, during insertion of the lead into a body, the helix is preferably retracted into the bore of the header 3 having a tubular shape in the distal end. In addition to a tip electrode in form of the helix, which is adapted to be screwed into the tissue, the lead comprises, as is mentioned above, a second electrode in form of the ring electrode 5 on a short distance from the distal end.

In the proximal end, the connecting structure 1 for connection to a not shown monitoring and/or controlling device comprises first and second sealing members 6 of an elastic material, in order to achieve a fluid tight connection to a socket recess of the monitoring and/or controlling device. In the area between the sealing members, the lead is provided with first 7 and second 7' electrically conducting connectors, which are adapted to be electrically coupled to mating connectors inside the monitoring and/or controlling device. The first connector 7, i.e. the most proximal connector, is in electrical contact with the helix 4, whereas the second connector 7' is in electrical contact with the ring electrode 5 by means of one or more electrically conducting coils inside the lead, as is to be explained more in detail below. In the most proximal end, the lead is provided with a rotatable pin 8 by means of which the helix 4 can be rotated and screwed out from the bore inside the header 3 and into the tissue.

Now reference is made to FIGS. 3 and 4, in which are illustrated a first embodiment of the flexible lead part 2 in a longitudinal section as well as a cross section through the lead, respectively. The lead has an inner tubular torque transferring member 9, an inner fluid tight tubing 10, an electrically conducting coil 11 and an outer fluid tight tubing 12. The inner tubular torque transferring member is rotatable arranged inside the inner tubing and is formed as a coil of five comparatively thick and rigid helical wires of e.g. metal or polymer, such that it is well suited for transferring of a torque from the proximal to the distal end of the lead. Moreover, the torque transferring member 9 defines an inner bore 13 for the purpose of allowing insertion of a guide wire or the like for guiding the tip of the lead to a desired position inside a body. The electrically conducting coil 11 is composed of two separate, co-radially wound wires 14, 14', each having an electrically conducting core 15 and a surrounding electrically insulating layer 16, such that they form two electrically separated inductance coils.

With reference also to FIG. 2, it is to be understood that the structure of the flexible lead part 2 as illustrated in FIGS. 3 and 4, extends from the connecting structure 1 in the proximal end to the header 3 in the distal end. Moreover, the tubular torque transferring member 9 is in its proximal end mechanically connected to the rotatable pin 8 and in its distal end mechanically connected to the helix 4, such that by rotating the rotatable pin it is possible to rotate the helix and extend it out from the inner bore of the header and screw it into the tissue. One of the wires in the electrically conducting coil 11 is in its proximal end electrically connected to the first connector 7 and in its distal end electrically connected to the helix 4, whereas the other wire in the electrically conducting coil is in its proximal end electrically connected to the second connector 7' and in its distal end electrically connected to the ring electrode 5.

Reference is then made to FIGS. 5 and 6, in which are illustrated a second embodiment of the flexible lead part 2 in a longitudinal section as well as a cross section through the lead, respectively. As in the first embodiment according to FIGS. 3 and 4, this embodiment comprises an inner tubular torque transferring member 9, formed of five helical wires in a similar way as in the first embodiment, and an inner fluid tight tubing 10. However, this embodiment includes two separate electrically conducting coils, one inner 17 and one outer 17', separated by an intermediate fluid tight tubing 18. Each of the electrically conducting coils is formed of one single wire 14, 14' having an electrically conducting core 15 and a surrounding electrically insulating layer 16, such that they form two coaxially arranged inductance coils. Also this embodiment comprises an outer fluid tight tubing 12.

As in the first embodiment, the tubular torque transferring member 9 is in its proximal end mechanically connected to the rotatable pin 8 and in its distal end mechanically connected to the helix 4, such that by rotating the rotatable pin it is possible to rotate the helix and extend it out from the inner bore of the header and screw it into the tissue. The inner electrically conducting coil 17 is in its proximal end electrically connected to the first connector 7 and in its distal end electrically connected to the helix 4, whereas the outer electrically conducting coil 17' is in its proximal end electrically connected to the second connector 7' and in its distal end electrically connected to the ring electrode 5.

Figure 8:
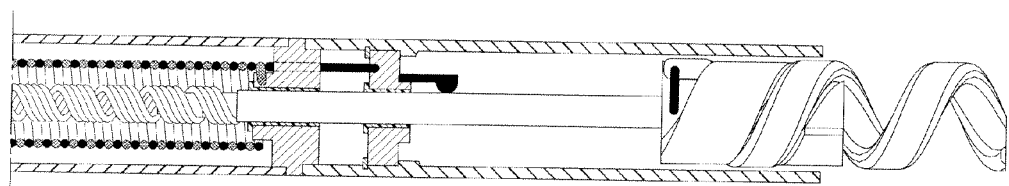
FIG. 8 is a longitudinal section according to FIG. 7 with the helix in an extended state.

Reference is then made to FIGS. 7 and 8 of the drawings, in which is illustrated a first embodiment of a connection of the electrically conducting wires 14, 14' to the electrodes as well as the tubular torque transferring member 9 to the helix 4. FIGS. 7 and 8 are longitudinal sections through the distal portion of a medical implantable lead, according to the embodiment as illustrated and described in relation to FIGS. 3 and 4, with the helix being retracted and extended, respectively.

The longitudinal sections of FIGS. 7 and 8 are taken at the joint between the header 3, as seen to the right, and the distal end portion of the flexible lead part 2 as illustrated in FIGS. 3 and 4. The header is made of a rigid material such as metal or a polymer and is formed with an inner bore 19, in which the helix 4 is rotatably and displaceably accommodated. In the joint region between the header and flexible lead part, the electrically conducting ring electrode 5 is provided, which also functions as a joint connector in that it comprises a distal shoulder surface, in which the proximal end of the header 3 is located and attached, and a proximal shoulder surface in which the distal end of the flexible lead part 2 is located and attached. At a short distance toward the distal end from the ring electrode 5, the lead is provided with a fixed support member 20. Both the ring electrode 5 and the support member 20 are formed with a through bore, through which a shaft 21 is rotatably and displaceably inserted, in the distal end of which the helix 4 is mounted. The shaft 21 is of an electrically conducting material and to prevent electrical connection between the shaft 21 and the ring electrode 5 as well as the support member 20, in case it is manufactured of an electrically conducting material, electrically insulating shaft bushings 22 are arranged in each of the through bores. To allow rotation and displacing of the helix 4 out from and into the inner bore 19 of the header, the tubular torque transmitting member is mechanically connected to the proximal end of the shaft. In case the tubular torque transferring member 9 is of an electrically conducting material, it may be advisable to arrange the connection in an electrically non-conducting fashion, such as via an electrically insulating sleeve 23 or the like. The electrically conducting coil of the lead comprises two electrically conducting wires 14, 14', which are electrically insulated from each other. To accomplish electrical connection to each of the ring electrode 5 and the helix 4, one of the electrical conducting wires 14' is electrically connected to the ring electrode 5, whereas the other electrically conducting wire 14 is electrically connected to a sliding contact 24 arranged on the support member 20, the sliding contact being in permanent electrically contact with the shaft 21, which is in electrically contact with the helix 4. In this way an electrical connection is ensured with the helix in spite of the fact that the tubular torque transferring member 9 is not electrically conducting and irrespective of the rotated and extended position of the helix.

Figure 9:
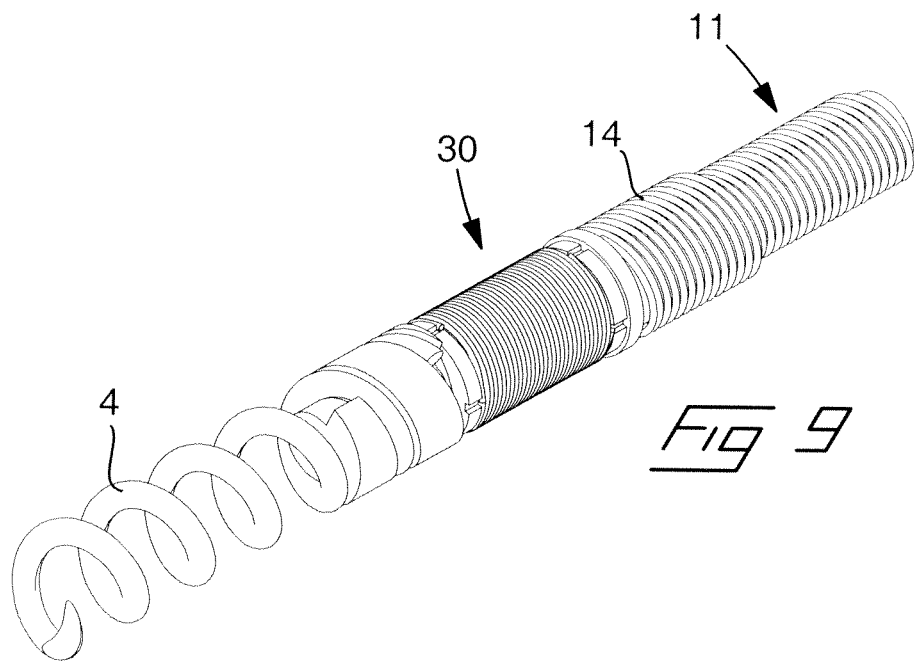
FIG. 9 is a perspective view of the distal end of the lead with the header removed and the helix in a retracted state, illustrating a second embodiment of the invention.
Figure 10:
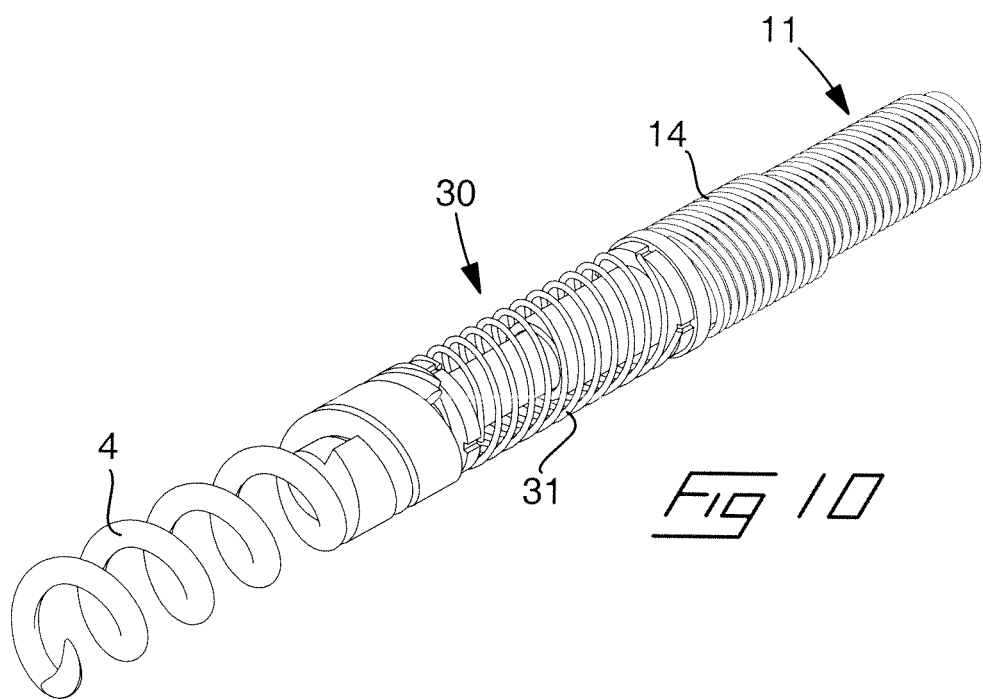
FIG. 10 is a perspective view according to FIG. 9 with the helix in an extended state.
Figure 11:
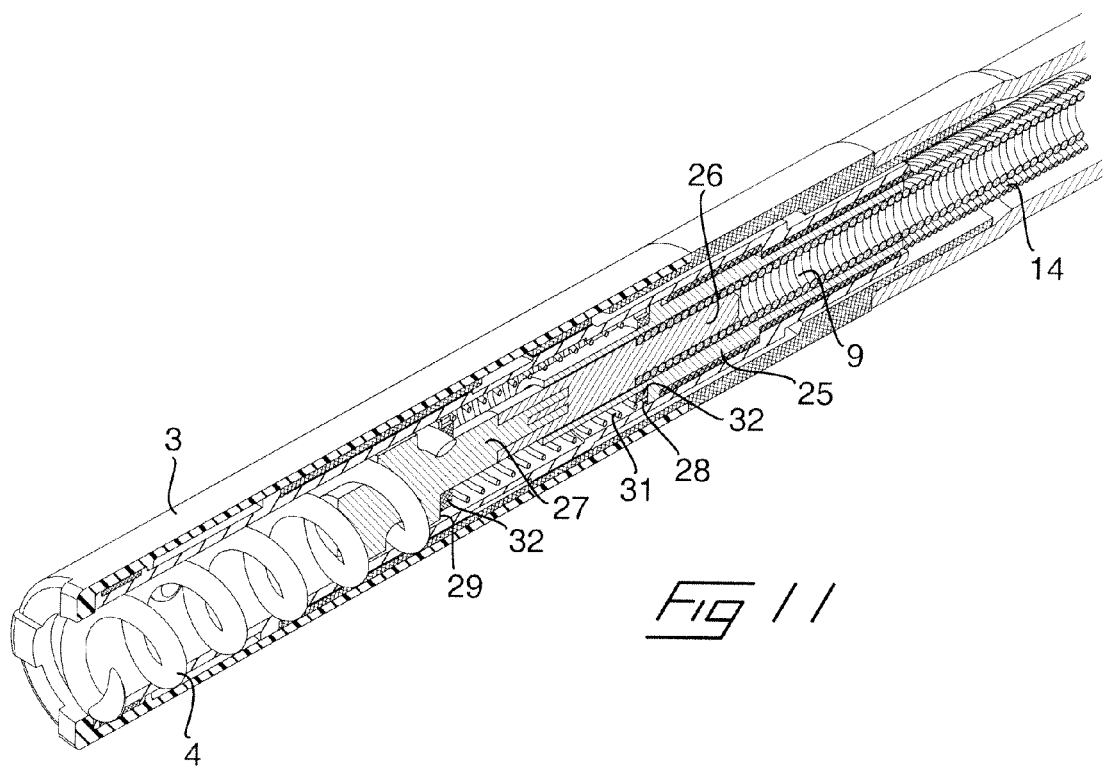
FIG. 11 is a cut through perspective view of the distal end of the complete lead according to FIGS. 9 and 10 with the helix in a retracted state.

Reference is then made to FIGS. 9 to 11 in which is illustrated a second embodiment of a connection of the wires 14 of the electrically conducting coil 11 to the helix 4. FIGS. 9 and 10 are perspective views of the inner parts of the lead whereas FIG. 11 is a cut through perspective view showing also the header 3 and the outer fluid tight tubing 12. As is best seen in FIG. 11, the lead is provided with a none rotating coupling 25 of an electrically conducting material which is formed with a through bore. A shaft carrying the helix is rotatable and displaceable mounted inside the through bore. Moreover, the shaft is composed of two different parts, i.e. a proximal part 26 of an electrically insulating material and a distal part 27 of an electrically conducting material. The coupling 25 is forming an annular shoulder surface 28 facing in the distal direction, whereas the distal part of the shaft is forming an annular shoulder surface 29 facing in the proximal direction. In a space formed between the shoulder surfaces of the coupling and the shaft, a wire assembly 30 of helically wound wires 31 is mounted. The wire assembly is composed of four electrically insulated wires which are attached at each end to an annular washer 32 and the wires are wound in counter clockwise direction around the axis of the shaft 26, 27. The annular washers are galvanically attached to the coupling 25 and the distal part 27 of the shaft, respectively, e.g. by means of welding or the like. When the helix 4 is retracted into the header 3, as in FIGS. 9 and 11, the wires 31 of the wire assembly 30 are each wound about five turns in the counter clockwise direction. When the helix subsequently is extended out from the header by being rotated in the clockwise direction, as in FIG. 10, the wire assembly 30 will be twisted in the clockwise direction such that the wires 31 in the wire assembly will simultaneously be unwound. Accordingly, the diameter reduction of the wire assembly due to the extending of the helix 4 will be counteracted by a diameter increment due to unwinding of the wires of the wire assembly.

Figure 12:
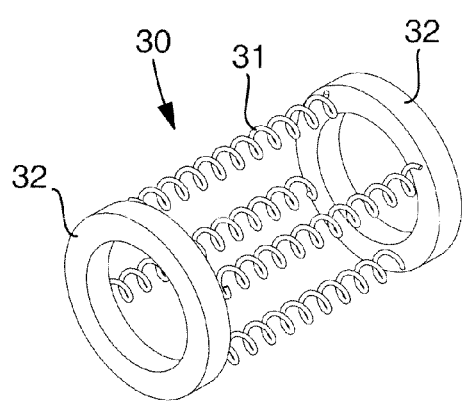
FIG. 12 is a perspective view of an alternative embodiment of an arrangement of helically wound wires for an electrical connection according to FIGS. 9 to 11.

In FIG. 12 is illustrated an alternative embodiment of the wire assembly 30. Also here the wire assembly is composed of four electrically insulated and conducting wires 31, which each are attached with their ends to an annular washer 32, respectively. However, in this embodiment the wires are not helically wound around an axis of the wire assembly but each wire only around itself such that the four helically wound wires will be parallel to each other when mounted in the lead. When extending the helix by rotation, each helical wire will be extended by stretching out the helical winding.

It is to be understood that the wire assembly can be formed also in many other ways than has been described and illustrated herein. For example, the wire assembly may be composed of only one or any other arbitrary number of electrical wires. Moreover, it is not absolutely necessary that the wire assembly comprises two annular washers in which the ends of the wires are attached. Instead, the wire ends could be attached directly to the coupling and the shaft, respectively. Also, it would be possible to use uninsulated wires instead of insulated if it is ensured that the wires will not come into contact with other electrically conducting parts of the lead, such as an electrically conducting header sleeve or the like. However, an electrically insulated helically wound wire is also advantageous for preventing induction of current from an electromagnetic field into the wire, as is described hereinbefore.

Although modifications and changes may be suggested by those skilled in the art, it is the intention of the inventors to embody within the patent warranted heron all changes and modifications as reasonably and properly come within the scope of their contribution to the art.

We claim as our invention:

1. An MRI-compatible medical implantable lead being adapted to be implanted into a human or animal body for monitoring and/or controlling of an organ inside the body, comprising:
    a lead body;
    a rotatable control member in a proximal end of the lead body;
    a tubular torque transferring member connected to the rotatable control member;
    a combined fixation structure and electrode member formed as a helix arranged in a distal end of the lead body to be rotatable in relation to the lead body and extendable out from the distal end of the lead body by rotation of the tubular torque transferring member, and which is configured to fix the distal end of the lead body to the organ by being screwed into the tissue by rotation of the control member and the tubular torque transferring member;
    a connector in the proximal end of the lead body;
    a stationary electrically conducting coil, which is separate from the tubular torque transferring member, the stationary electrically conducting coil comprising one or more individual wires each comprising an electrically conducting wire core and a surrounding electrically insulating layer;
    at least one helically wound wire electrically connecting the stationary electrically conducting coil and the helix to enable transfers of electrical signals between the electrically conducting coil and the helix irrespective of the rotational position of the helix wherein the connector is electrically coupled to helix by the stationary coil and the helically wound wire and wherein the tubular torque transfer member is electrically isolated from the helix;
    a non-rotating coupling formed of electrically conducting material, the non rotating coupling being electrically coupled to the stationary electrically conducting coil; and
    a shaft having an electrically conductor distal end electrically coupled to the helix, the shaft being configured to mechanically interconnect the helix and the tubular torque transferring member, wherein the non-rotating coupling includes a bore configured to receive the shaft and wherein the at least one helically wound wire electrically connects the non-rotating coupling and an electrically conducting distal part of the shaft.

2. A medical implantable lead according to claim 1, wherein the tubular torque transferring member is formed as a coil comprising one or more helical wires.

3. A medical implantable lead according to claim 2, wherein the wires of the tubular torque transferring member are metallic.

4. A medical implantable lead according to claim 2, wherein the wires of the tubular torque transferring member are comprised of an electrically non-conducting material.

5. A medical implantable lead according to claim 1, wherein the tubular torque transferring member is formed as a flexible tubing.

6. A medical implantable lead according to claim 1, further comprising a ring electrode and wherein the one or more individual wires of the stationary electrically conducting coil comprise two electrically conducting coils coaxially arranged in relation to each other and wherein a first one of the individual wires is electrically coupled to the ring electrode and a second one of the individual wires is electrically connected to the helix.

7. A medical implantable lead according to claim 1, wherein the helically wound wire has a direction of thread contrary to a direction of rotation when extending the helix.

8. A medical implantable lead according to claim 1, wherein the helically wound wire is formed as a unitary wire assembly.

9. A medical implantable lead according to claim 8, wherein the wire assembly is formed of helically wound wires arranged in parallel to each other.

10. A medical implantable lead according to claim 1, wherein the shaft comprises the electrically conducting distal part mechanically and electrically connected to the helix and an electrically insulating proximal part mechanically connected to the electrically conducting distal part and the tubular torque transferring member.

11. A medical implantable lead according to claim 1, further comprising a first annular washer galvanically attached to the coupling and a second annular washer galvanically attached to the electrically conducting distal part, the at least one helically wound wire being attached to the first annular washer and the second annular washer.

* * * * *